US009395557B2

(12) United States Patent
Thompson

(10) Patent No.: US 9,395,557 B2
(45) Date of Patent: Jul. 19, 2016

(54) PARTIAL CORNEAL CONJUNCTIVAL CONTACT LENS

(71) Applicant: Vance M. Thompson, Sioux Falls, SD (US)

(72) Inventor: Vance M. Thompson, Sioux Falls, SD (US)

(*) Notice: Subject to any disclaimer, the term of this patent is extended or adjusted under 35 U.S.C. 154(b) by 0 days.

(21) Appl. No.: 14/539,652

(22) Filed: Nov. 12, 2014

(65) Prior Publication Data

US 2016/0131924 A1    May 12, 2016

(51) Int. Cl.
*G02C 7/04* (2006.01)
(52) U.S. Cl.
CPC .......................... *G02C 7/04* (2013.01)
(58) Field of Classification Search
CPC ....... G02C 7/04; G02C 7/049; G02C 2202/16
USPC .............. 351/159.02, 159.04, 159.73, 159.78
See application file for complete search history.

(56) References Cited

U.S. PATENT DOCUMENTS

| | | | |
|---|---|---|---|
| 2,641,161 A | 6/1953 | Silvertstein | |
| 3,973,838 A * | 8/1976 | Page | G02C 7/04 351/159.7 |
| 4,157,864 A * | 6/1979 | Koller | G02C 7/04 351/159.02 |
| 4,194,815 A | 3/1980 | Trombley | |
| 4,353,849 A | 10/1982 | Lewison | |
| 4,652,099 A * | 3/1987 | Lichtman | G02C 7/046 351/159.24 |
| 5,929,968 A | 7/1999 | Cotie et al. | |
| 7,249,849 B2 | 7/2007 | Marmo et al. | |
| 7,559,649 B2 | 7/2009 | Cotie et al. | |
| 8,118,426 B2 | 2/2012 | Cotie et al. | |
| 8,459,793 B2 | 6/2013 | de Juan, Jr. et al. | |
| 8,506,944 B2 | 8/2013 | Sullivan et al. | |
| 2010/0092452 A1 | 4/2010 | Sullivan et al. | |
| 2010/0233241 A1 | 9/2010 | Leahy et al. | |
| 2011/0059902 A1 | 3/2011 | Sullivan et al. | |
| 2011/0070222 A1 | 3/2011 | Sullivan et al. | |
| 2011/0142908 A1 | 6/2011 | Sullivan et al. | |
| 2011/0184358 A1 | 7/2011 | Weiner et al. | |
| 2012/0321611 A1 | 12/2012 | Sullivan et al. | |
| 2013/0077044 A1 | 3/2013 | de Juan, Jr. et al. | |

FOREIGN PATENT DOCUMENTS

| | | |
|---|---|---|
| CA | 2 539 395 A1 | 4/2005 |
| CA | 2 539 395 C | 9/2013 |
| EP | 2 276 496 | 1/2011 |

(Continued)

OTHER PUBLICATIONS

Ciolino et al., "In vivo performance of a drug-eluting contact lens to treat glaucoma for a month", Biomaterials, 35 (2014), 432-439.

(Continued)

*Primary Examiner* — Darryl J Collins
(74) *Attorney, Agent, or Firm* — Patterson Thuente Pedersen, P.A.

(57) ABSTRACT

A contact lens system, including a peripheral conjunctival cover portion including a shell curved and sized to substantially overly a conjunctiva of an eye. The conjunctival cover portion defines a full thickness central opening therethrough. The central opening is positioned within the conjunctival cover and sized to expose at least a portion of a cornea of the eye. The contact lens system further includes a central contact lens portion that is substantially equivalent in size to the central opening and positioned or positionable at the central opening.

14 Claims, 13 Drawing Sheets

(56) References Cited

FOREIGN PATENT DOCUMENTS

| | | |
|---|---|---|
| EP | 2 276 497 | 1/2011 |
| EP | 2 632 532 | 9/2013 |
| WO | WO 01/33284 A1 | 5/2001 |
| WO | WO 2004/109368 A2 | 12/2004 |
| WO | WO 2005/121874 A1 | 12/2005 |
| WO | WO 2007/008666 A2 | 1/2007 |
| WO | WO 2009/137602 A1 | 11/2009 |
| WO | WO 2009/137603 A1 | 11/2009 |
| WO | WO 2010/105130 A2 | 9/2010 |
| WO | WO 2011/050287 A1 | 4/2011 |
| WO | WO 2012/058382 A2 | 5/2012 |

OTHER PUBLICATIONS

Severinsky et al., "Curent applications and efficacy of sclera contact lenses—a retrospective study", 2010, 5 pages.

"Innovative drug-dispensing contact lens delivers glaucoma mediation continuously for a month", Ophthalmology, Dec. 9, 2013, 2 pages.

"Piggyback Lens" for Advanced Keratoconus, prior to Dec. 6, 2013, pp. 18-19.

* cited by examiner

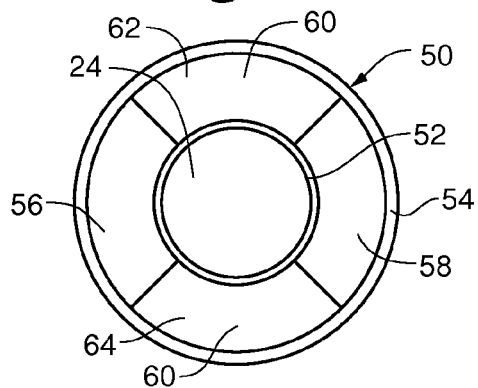
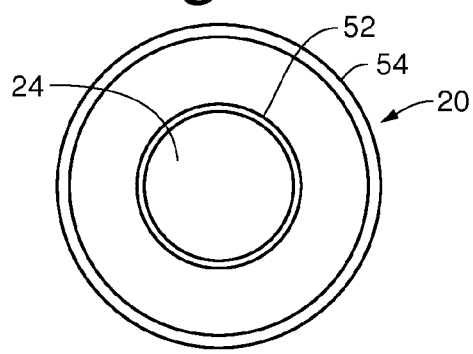
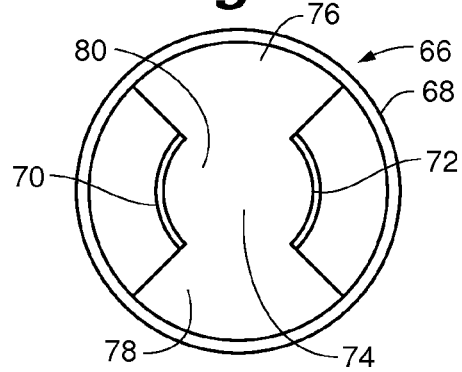

PARTIAL CORNEAL CONJUNCTIVAL CONTACT LENS

FIELD OF THE INVENTION

The invention relates generally to the field of contact lenses and to the field of medication delivery by inserts.

BACKGROUND OF THE INVENTION

Contact lenses have been in existence for many decades. Early contact lenses were made of glass or rigid plastic such as polymethylmethacrylate (PMMA). Early contact lens designs were quite large and referred to as scleral or haptic lens. Scleral or haptic contact lens designs cover the cornea completely as well as covering a large portion of the conjunctiva or sclera of the eye. The sclera is the structural white of the eyeball while the conjunctiva is a transparent tissue which overlies the sclera as well as covering the backside of the eye lids. Early contact lens designs were made of rigid, largely oxygen impermeable polymers as discussed above or a very few of glass. Because cornea physiology was poorly understood at the time these lenses were made, they often cause great discomfort and negative effect on the corneal health.

As time went by, in the 1950's, hard contact lenses made of polymethylmethacrylate became much smaller having a diameter significantly smaller than that of the cornea. Hard corneal contact lenses were more comfortable and less physiological damaging than scleral or haptic lenses, but only marginally so. Hard contact lenses still significantly deprived the cornea of a necessary oxygen supply from atmospheric oxygen to maintain good corneal health and were difficult to adapt to. In the 1970s, so called soft corneal contact lenses became available. Soft contact lenses generally are larger than hard corneal contact lenses having a diameter approximating that of the cornea, somewhat larger than the cornea or somewhat smaller than the cornea. Soft contact lenses are generally made of hydrophilic polymers, such as polyhydroxy ethylmethacrylate (poly HEMA), that absorb substantial amounts of water, saline solution or the tear film. Soft contact lenses also provided improved comfort due to their permeability to oxygen and due to their more flexible nature. Later still, so called gas-permeable contact lenses became available. Gas permeable rigid contact lenses are similar in size and structure to hard corneal contact lenses but are made of rigid oxygen permeable polymers that allow oxygen and other gases to pass through the material of the contact lens to provide improved corneal health. Generally, rigid contact lenses provide sharper vision than soft contact lenses though this is not universally true.

Hard contact lenses are well as scleral or haptic contact lenses were sometimes fenestrated. That is, tiny holes were drilled or otherwise formed through the rigid contact lens material in an effort to improve tear exchange under the contact lens or to provide a greater availability of oxygen through the contact lens. Fenestration was generally not a very successful technique. Fenestrations, however, were uniformly tiny holes generally much smaller than one millimeter in diameter, occasionally multiple fenestrations were present.

All contact lenses known to the applicant provide substantially or complete coverage of the cornea of the eye.

Drug delivery inserts are also known to exist. Drug delivery inserts are small containers into which drugs or pharmaceuticals are placed or absorbed that exist in several different forms. Subpalpebral drug delivery inserts are generally intended to be inserted behind the eye lid in the conjunctival fornices and to gradually release a desired medication to provide a slow, continuous supply of drug to the eye. Subpalpebral drug delivery inserts generally have suffered from being uncomfortable for the patient to tolerate and subject to be accidentally dislodged from the eye by rubbing of the eye or other movements. In addition, subpapebral drug delivery inserts sometimes cause irritation of the conjunctiva or the eye lids.

Another variety of drug delivery insert is intended to be surgically inserted within the globe of the eye to gradually leach out a steady supply of a desired drug into the intraocular environment. Intraocular drug delivery inserts are less often used due to their relatively invasive nature.

Generally, drug delivery inserts whether subpalpebral or intraocular have contained a single drug.

Dry eye syndrome is one of the most commonly treated eye problems in the United States. Dry eye syndrome is also known as keratitis sicca, keratoconjunctivitis sicca (KCS) xerophthalmia, and lacrimal insufficiency. It is estimated that over ten million Americans and 30 million persons worldwide suffer from dry eye syndrome.

For a large fraction of dry eye patients, dry eye syndrome creates discomfort or annoyance. For those severely afflicted, dry eye syndrome can be debilitating and, in some circumstances, even sight-threatening. In extremely severe cases, dry eye syndrome can even lead to the loss of an eye.

Dry eye syndrome typically results from deficiency in the quality or quantity of tears produced by the patient. Precorneal tear film has traditionally been considered to have a three-layered structure. Closest to the cornea lies the mucin, or mucus, layer. The mucin layer provides an interface between the corneal epithelium and the remainder of the tear film. Overlying the mucin layer is the watery aqueous layer, which is the thickest layer of the three. The outermost layer of the precorneal tear film is the lipid layer. The lipid layer is an oily film that reduces evaporation from the aqueous layer beneath it.

The middle aqueous layer provides moisture to the corneal tissue, carries important nutrients, and serves to remove metabolic waste produced by the cornea. Deficiency in any of the three layers of the precorneal tear film can result in complaints of dry, gritty feeling or burning eyes.

The mucin that forms the mucin layer, nearest the cornea, is secreted by goblet cells in the conjunctiva. The conjunctiva is the transparent tissue that covers the sclera and the backside of the eyelids. The mucin layer functions to decrease surface tension of the tear film. In addition, the cornea itself is hydrophobic. Without the mucin layer to provide a bridge between the cornea and the aqueous layer, the aqueous layer would bead up and allow dry spot formation on the cornea.

The aqueous layer is secreted primarily by the glands of Wolfring and Krause located in the eyelid margin. The aqueous layer helps provide an optically smooth, transparent surface to the precorneal tear film. The lipid layer is secreted by the meibomian glands, and the glands of Zeiss and Moll. The glands of Zeiss and Moll are also located at the eyelid margin.

Blinking is essential to maintenance of the precorneal tear film. During each blink, the eyelid wipes over the surface of the cornea, smoothing the mucin layer and spreading the overlying aqueous and lipid layers to provide a completely wetted surface. In between blinks, the tear film thins due to evaporation of the aqueous layer. If evaporation is excessive, dry spots may form on the surface of the cornea.

Deficiency, or imperfect quality, of any of the three component layers can lead to dry eye symptoms. Many systemic and external factors can contribute to dry eye syndrome. For example, Sjogren's syndrome is associated with arthritic diseases in combination with dry eye and dry mouth. Deficiency of Vitamin A, use of oral contraceptives and environmental factors can all contribute to dry eye syndrome. Inflammation has also been demonstrated to contribute to dry eye.

Research into the natural history of dry eye syndrome suggests that the disease progresses through four stages. Each stage is a consequence of the preceding stage. The stages are:
1. Loss of water from the aqueous layer of the tear film leading to an increase in the tear film osmolarity;
2. Loss of conjunctival goblet cells and decreased corneal glycogen;
3. Increased loss of corneal squamous epithelial cells;
4. Destabilization of the interface between the corneal surface and the tear film.

Either decreased secretion of tear film components or increased evaporation lead to increased tear film osmolarity and the following stages that lead to eventual corneal decompensation and the serious consequences of dry eye syndrome.

The adnexa of the eye may also be involved in dry eye syndrome. The adnexa of the eye include the structures surrounding the eye such as the eyelids, eye lashes, the tear drainage and tear production structures. Blepharitis commonly contributes to dry eye syndrome. Blepharitis typically results from bacterial infection of the tiny glands in the margin of the eyelid. These glands include the glands of Zeiss, Moll and Wolfring as well as the meibomian glands. Most commonly, the affected glands are the meibomian glands. In bacterial blepharitis, bacterial infection causes the meibomian glands to become plugged, and thus not be able to produce a normal lipid layer to contribute to the tear film. Some bacteria that infect the glands also secrete exotoxins that seep out of the glands into the eye and injure the corneal epithelium.

Treatments of dry eye syndrome vary depending upon the type of presentation. The most common treatment for dry eye syndrome is the use of artificial tear supplements to provide additional moisture and lubrication to the corneal surface. Artificial tear eye drops are placed on the eye by the patient. Artificial tear supplements must be used regularly and often to be effective.

Lubricant ointments may also be employed. Ointments are usually used at bedtime because they tend to be messy and blur vision. For some patients, even the use of ointments is not sufficient to provide comfort during sleep.

Tears drain from the eye through the lacrimal drainage system. Tiny openings at the nasal corner of each upper and lower eyelid are called the lacrimal puncta. The lacrimal puncta lead into ducts that drain into the nasopharynx.

One treatment for dry eye syndrome is to partially or completely close one or more lacrimal puncta to reduce tear outflow into the lacrimal drainage apparatus. Traditionally, this closure was accomplished surgically or by cautery. In the last decade, however, temporary and permanent punctal occlusion plugs have been utilized.

Permanent punctal plugs are typically made from surgical silicone; temporary plugs are generally made of soluble collagen. Collagen plugs dissolve over a period of days and are helpful in diagnosis.

Punctal plugs are placed into the lacrimal puncta, or lacrimal drainage ducts. The plugs impede the outflow of tears from the eye. This approach slows the outflow of tears and retains them in the eyes longer, often relieving symptoms. Punctal plugs have the distinct advantage of being readily removable and avoid the issues of scar formation.

Blepharitis is sometimes treated by the use of antibiotic medications. Another important treatment for blepharitis is the application of warm soaks and lid scrubs. In this form of treatment, the patient applies a warm wet washcloth to the eyelids for a period of time to provide humidity, warmth and to help soften blockage of and restore flow from the meibomian glands. Lid scrubs are practiced by taking a mild, non-irritating soap and vigorously scrubbing the eyelid margins with they eyes closed, so as to massage the meibomian glands and increase production. The surfactant helps to dissolve the greasy blockage of the meibomian glands.

Patients who have severe dry eye syndrome often suffer disrupted sleep because they cannot go for longer than an hour or so without applying tear supplements to the eyes. This can lead to pronounced sleep deprivation and a consequent reduction in quality of life.

A variety of researchers have been seeking other medicinal treatments for dry eye syndrome. Largely, this research is directed at pharmaceutical efforts to increase tear production.

Accordingly, there is still room for improvement in the contact lens related.

SUMMARY OF THE INVENTION

A partial corneal conjunctiva contact lens according to an example embodiment of the invention includes an annular conjunctival cover in combination with a central lens portion. The central lens portion may be physically separate and used along with the annular conjunctival cover on the eye or may be physically joined to the annular conjunctival cover. The central lens may be of size somewhat larger than a central opening of the annular conjunctival cover and overlap the annular conjunctival cover either anteriorly or posteriorly when the combination of central lens portion and than a central opening of the annular conjunctival cover is applied to the eye. Alternately, the central lens may be somewhat smaller in diameter than the central opening of the annular conjunctival cover and may be positioned within the opening when the central lens and annular conjunctival cover are applied to the eye. In this case the central lens may be a separate structure from the conjunctival cover or may be physically coupled to the annular conjunctival cover.

For the purposes of this application, reference may be made to the central lens portion or central contact lens portion being substantially equivalent in size to the central opening in the conjunctival cover. This term shall be defined as the central lens having an outside diameter equal to the inside diameter of the central opening or varying by plus or minus five millimeters.

According to another example embodiment the annular conjunctival cover and the central lens portion are joined as an integral unit with coupling members securing the central lens portion to the annular conjunctival cover and passages between the central lens portion and the annular conjunctival cover permitting fluid flow. The central lens portion may be somewhat larger than a central opening of the annular conjunctival cover and joined to the annular conjunctival cover to overlap the annular conjunctival cover either anteriorly or posteriorly. Thus, the central lens portion may overly or underlie the annular conjunctival cover when the central lens portion is placed on the eye. Alternately, the central lens may be somewhat smaller in diameter than the central opening of the annular conjunctival cover and be coupled within the opening of the annular conjunctival cover. Fluid patent passages that permit the flow of tears between the central lens portion and the annular conjunctival cover are present in each of the above described integral units.

The annular conjunctival cover in combination with the central lens portion is expected to facilitate tear pumping from the posterior space between the annular conjunctival cover and the central lens portion and the eye to the anterior surface of the annular conjunctival cover and the central lens portion.

According to another embodiment, the invention includes a method of treating or correcting a patient including applying a conjunctival cover having an opening centrally located therein to the eye and then applying a central contact lens portion over, under or within the opening in the conjunctival cover.

According to other embodiments of the invention, the central lens portion is coupled to the annular conjunctival cover overlying, underlying or within the central opening at multiple locations. For example, the central lens portion may be coupled adjacent the central opening of the annular conjunctival cover by three coupling members. According to another embodiment, the central lens portion may be coupled to the annular conjunctival cover by four or more coupling members. The coupling members may be arranged symmetrically around or adjacent the perimeter of the central lens portion or may be arranged asymmetrically. For example, three coupling members may be arranged at 120 degree angles around the perimeter of the central lens portion. According to another example embodiment, four coupling members can be arranged at 90 degrees intervals around the perimeter of the central lens portion. According to other embodiments of the invention, coupling members may be asymmetrically arranged. For example, in one embodiment, three coupling members may be arranged at 3 o'clock, 12 o'clock and 9 o'clock which two additional coupling members may be arranged at the 4 o'clock and 8 o'clock positions. The arrangement of coupling members, whether symmetrical or asymmetrical may have an effect on the pumping of tears as the blinking eyelid moves, compresses and releases the corneal conjunctival contact lens system.

BRIEF DESCRIPTION OF THE DRAWINGS

FIG. 5 is a schematic depiction of a conjunctival cover having an inner ring, an outer ring and a segmented structure according to an example embodiment of the invention;

FIG. 6 is a schematic depiction of an annular conjunctival cover according to an example embodiment of the invention;

FIG. 7 is a schematic depiction of a conjunctival cover having a partial inner ring, an outer ring and a segmented structure according to an example embodiment of the invention;

DETAILED DESCRIPTION

Figure 1:
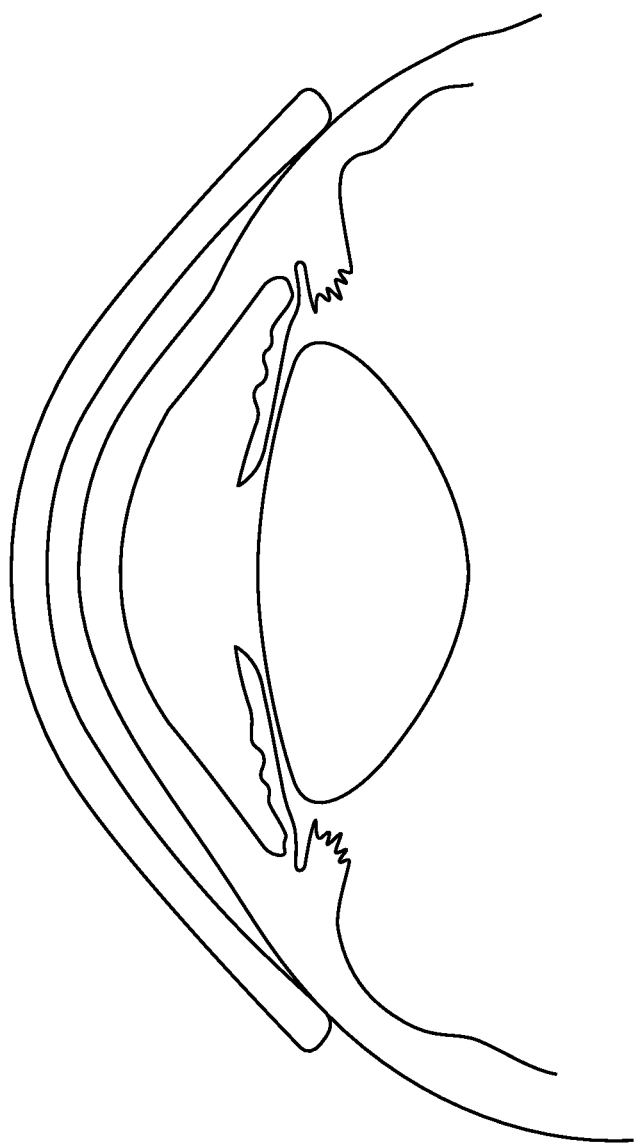
FIG. 1 is a schematic depiction of a prior art scleral contact lens.
Figure 2:
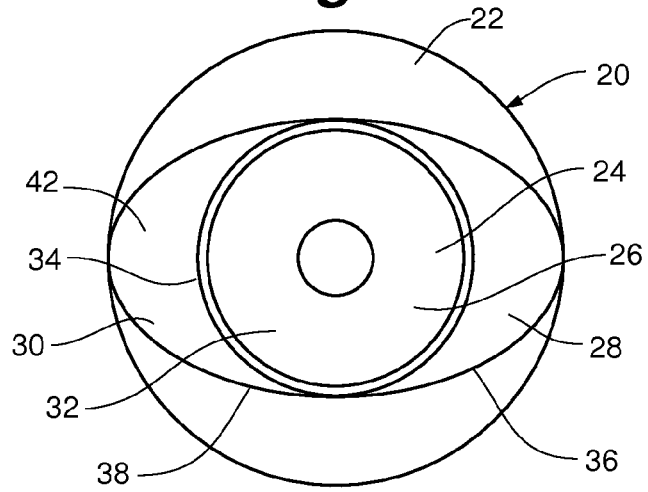
FIG. 2 is a schematic depiction of an annular conjunctival cover applied to an eye according to an example embodiment of the invention.

Referring to FIGS. 11-18, corneal conjunctival contact lens system 100 generally includes conjunctival cover 102 and central lens portion 104.

Conjunctival cover 102 is generally as described elsewhere in this application. Accordingly, conjunctival cover 102 of corneal conjunctival contact lens system 100 may take the form of conjunctival shield 20, elliptical conjunctival shield 46, dual ring conjunctival shield 50, partial inner ring conjunctival shield 66, drug delivery conjunctival shield 82 or multilayer conjunctival shield 92.

Accordingly, example embodiments of corneal conjunctival contact lens system 100 include uncoupled corneal conjunctival lens system 106 and coupled corneal conjunctival lens system 108.

Figure 11:
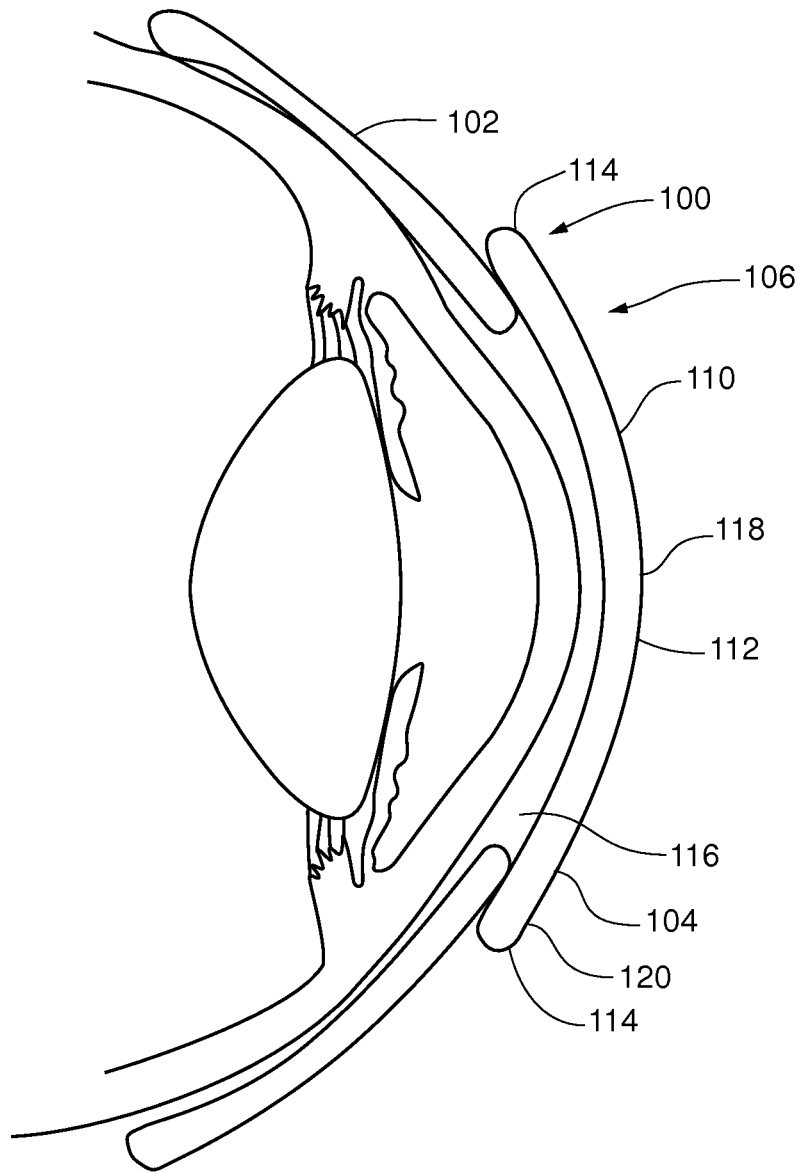
FIG. 11 is a cross-sectional view of an embodiment of the invention in situ on an eye including an annular conjunctival cover and a central lens portion overlying the annular conjunctival cover according to an example embodiment of the invention.
Figure 12:
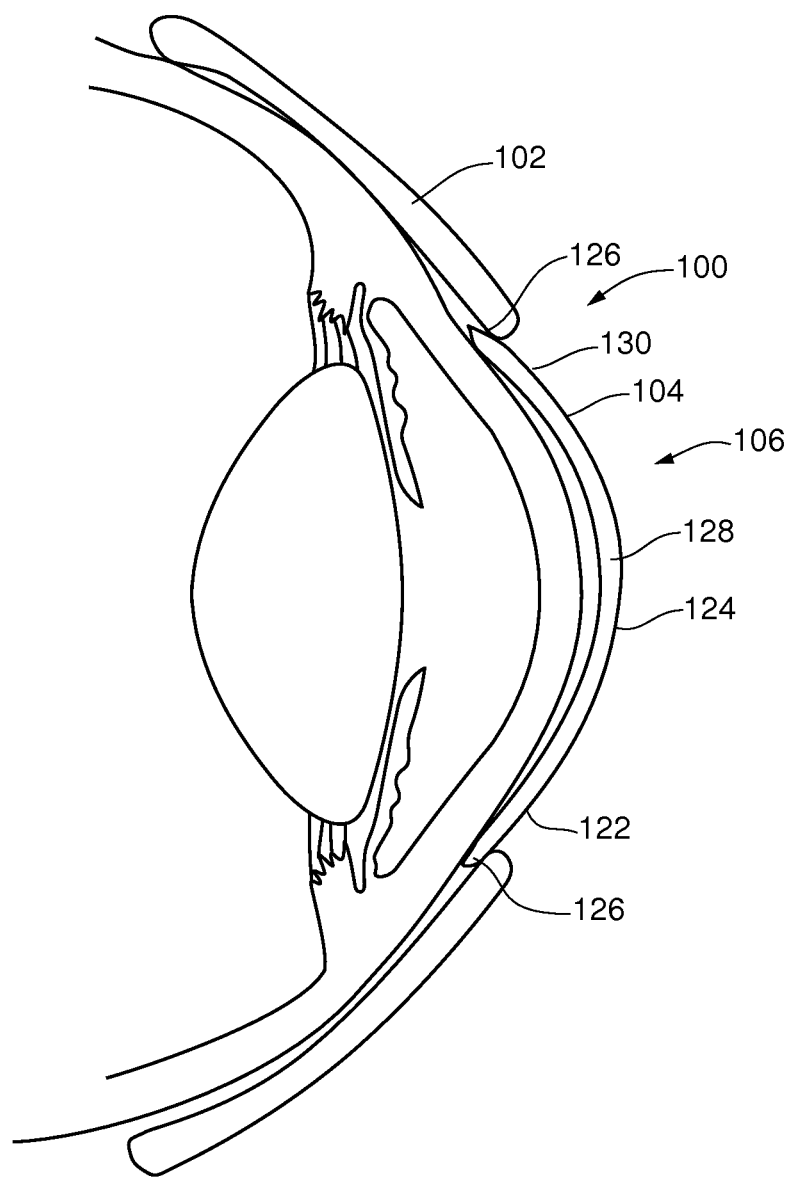
FIG. 12 is a cross-sectional view of an annular conjunctival cover in situ on an eye and a central lens portion underlying the annular conjunctival cover according to an example embodiment of the invention.
Figure 13:
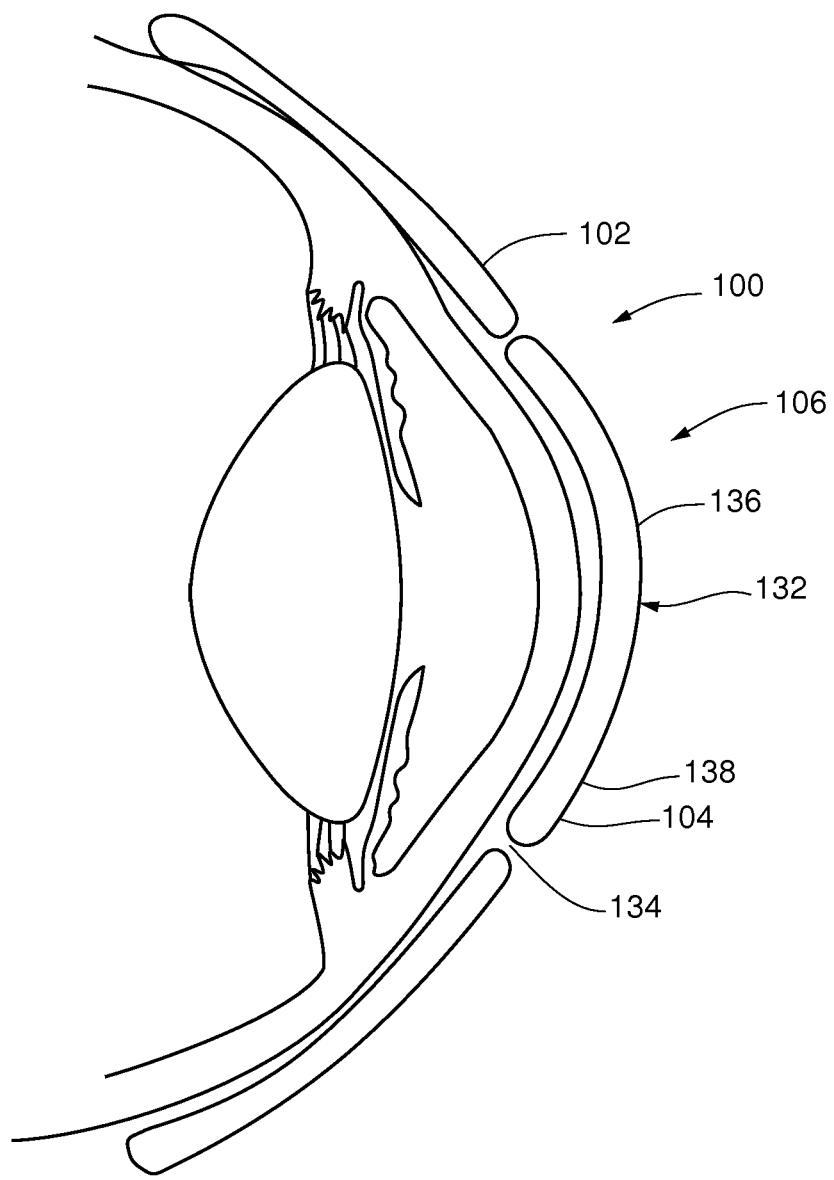
FIG. 13 is a cross-sectional view of an annular conjunctival cover and a central lens portion situated within the opening of the annular conjunctival cover in situ on an eye according to an example embodiment of the invention.

Referring particularly to FIGS. 11-13, uncoupled corneal conjunctival lens system 106 includes: conjunctival cover 102 and central lens portion 104 which are physically separate structures.

Referring to FIG. 11, uncoupled corneal conjunctival lens system 106 may include overlying central lens portion 110. According to this embodiment, conjunctival cover 102 is placed on the eye first, followed by overlying central lens portion 110. Overlying central lens portion 110 includes: bridging portion 112 and overlying portion 114. Overlying central lens portion 110 is movable with blinking relative to conjunctival cover 102. Accordingly, the margin between bridging portion 112 and overlying portion 114 is somewhat variable. Bridging portion 112 generally bridges over central opening 116 of conjunctival cover 102. Overlying central lens portion 110 may be similar in design to soft or rigid contact lens known to those of ordinary skill in the art. Overlying central lens portion 110 may also include features that distinguish bridging portion 112 from overlying portion 114. Overlying central lens portions 110 also generally includes a central optical zone 118 and a peripheral zone 120. Optical zone 118 may or may not coincide with bridging portion 112. Peripheral zone 120 may or may not coincide with overlying portion 114.

Referring now to FIG. 12, uncoupled corneal conjunctival lens system 106 including underlying central lens portion 122 is depicted. Underlying central lens portion includes opening portion 124 and underlying portion 126. Underlying central lens portion 122 also includes optical zone 128 and peripheral zone 130 similar to contact lens known to those of ordinary skill in the art. Optical zone 128 does not necessarily coincide with opening portion 124 nor does peripheral zone 130 necessarily coincide with underlying portion 126 though they may coincide.

Referring to FIG. 13 another embodiment of uncoupled corneal conjunctival lens system 106 is depicted. In the depicted embodiment, intraopening central lens portion 132 is sized to be somewhat smaller than central opening 134 of conjunctival cover 102. Intraopening central lens portion 132 is sized to be smaller than central opening 134. Intraopening central lens portion 132 may be similar in structure and design to conventional soft or rigid contact lens known to those of ordinary skill in the art. Intraopening central lens portion 132 generally includes optical zone 136 and peripheral zone 138.

Referring now to FIGS. 14-19, example embodiments of coupled corneal conjunctival lens system 108 are depicted. The depicted embodiments include conjunctival cover portion 140 and coupled central lens portion 142.

Figure 14:
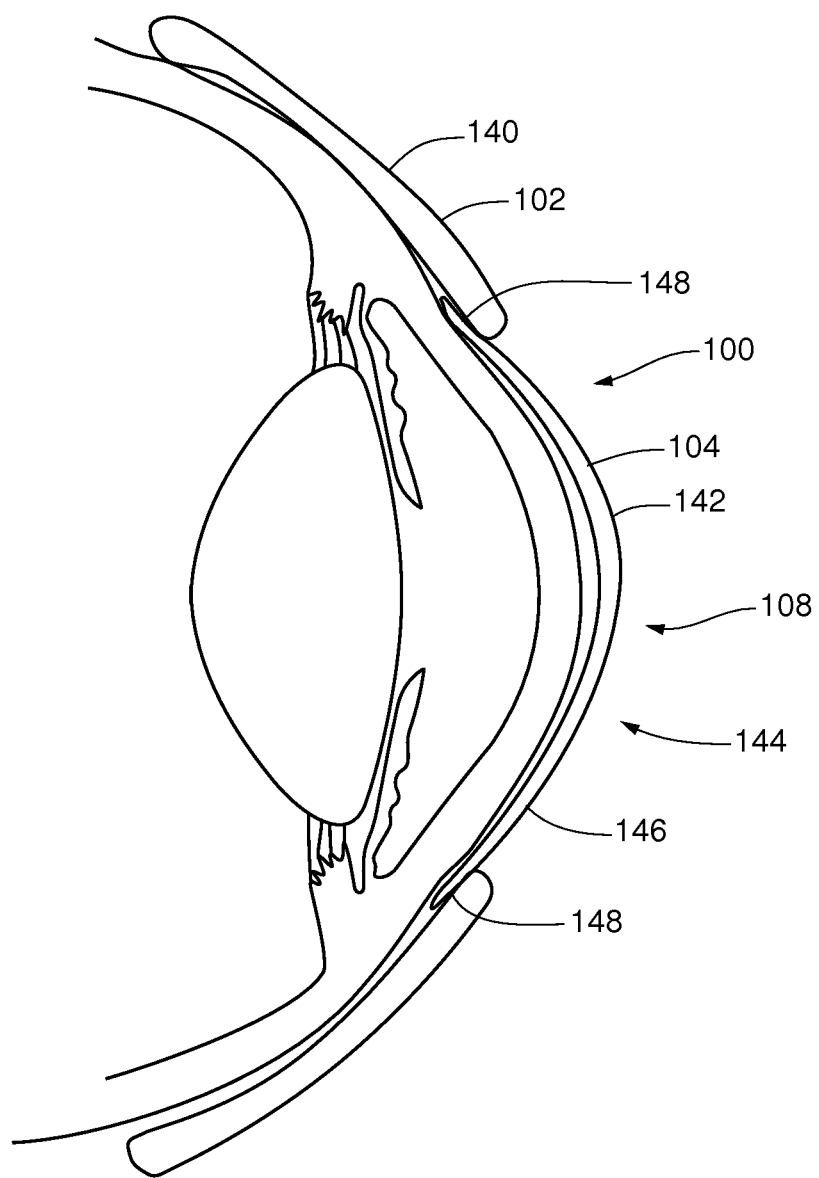
FIG. 14 is a cross-sectional view of an annular conjunctival cover and an attached central lens portion underlying the annular conjunctival cover in situ on an eye according to an example embodiment of the invention.
Figure 16:
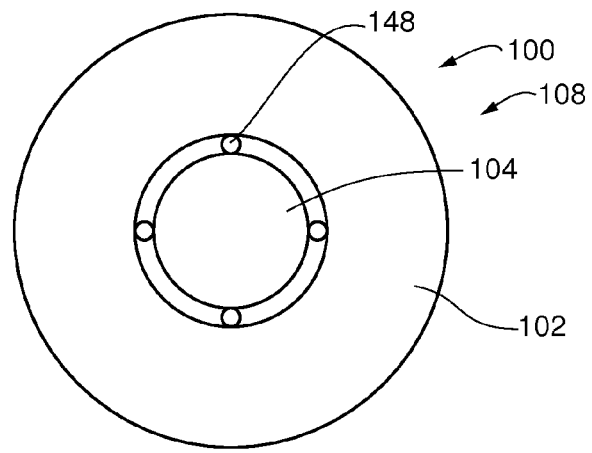
FIG. 16 is a schematic plan view of an annular conjunctival cover with an attached central lens portion secured to the annular conjunctival cover via four attachment numbers according to an example embodiment of the invention.
Figure 17:
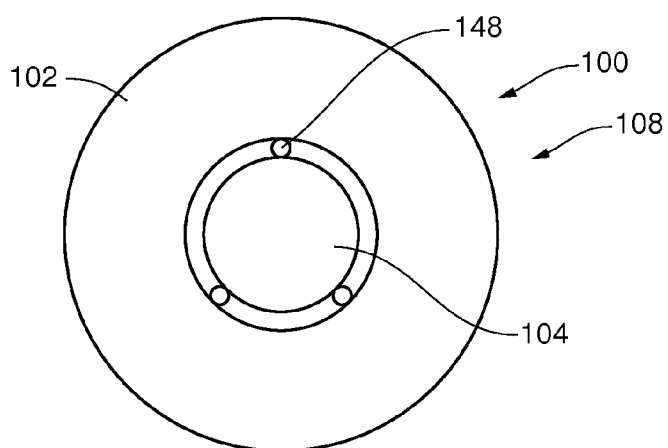
FIG. 17 is a schematic plan view of an annular conjunctival cover and an attached central lens portion coupled to the annular conjunctival cover by three symmetrically located attachment members according to an example embodiment of the invention.
Figure 18:
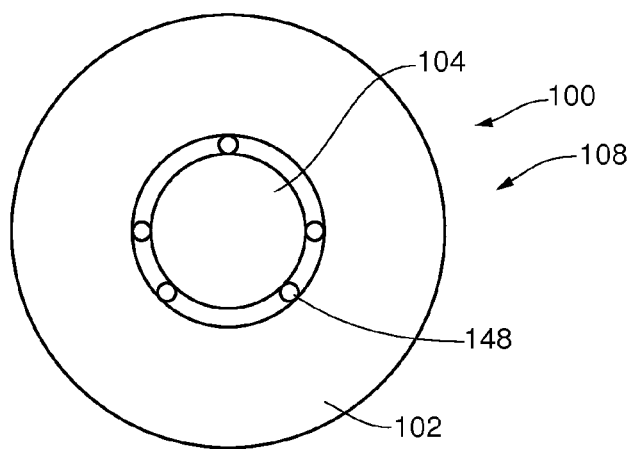
FIG. 18 is a plan view of annular conjunctival cover and an attached lens portion attached to the annular conjunctival cover by five asymmetrically located attachment members according to an example embodiment of the invention.

Referring now to FIG. 14, posterior coupled corneal conjunctival lens 144 includes conjunctival cover 102 and posterior central lens portion 146. Referring to FIGS. 14 and 16-18, posterior central lens portion 146 is attached to conjunctival cover 102 by attachment members 148. As depicted in FIGS. 16-18, attachment members 148 may be arranged symmetrically or asymmetrically. Attachment members 148 may also vary in size and shape from each other.

Figure 15:
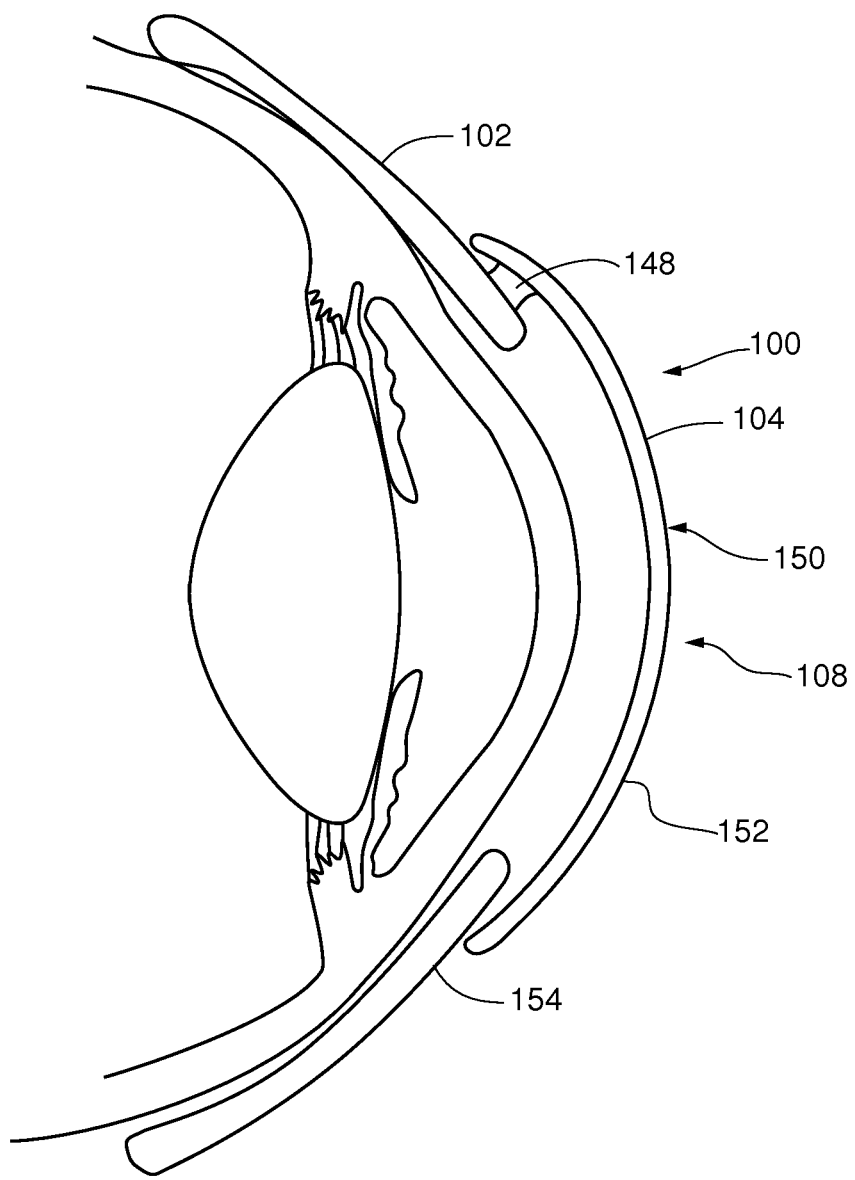
FIG. 15 is a cross-sectional view of an annular conjunctival cover with an attached central lens portion overlying the annular conjunctival cover in situ on an eye according to an example embodiment of the invention.

Referring now to FIG. 15, anterior coupled corneal conjunctival lens 150 is depicted. Anterior coupled corneal conjunctival lens 150 includes anterior central lens portion 152 coupled to conjunctival cover portion 154. Similar to the above described example embodiment, attachment members 148 may be oriented symmetrically or asymmetrically as depicted in FIGS. 16-18. Further, attachment members 148 may vary in size and shape relative to one another.

Figure 19:
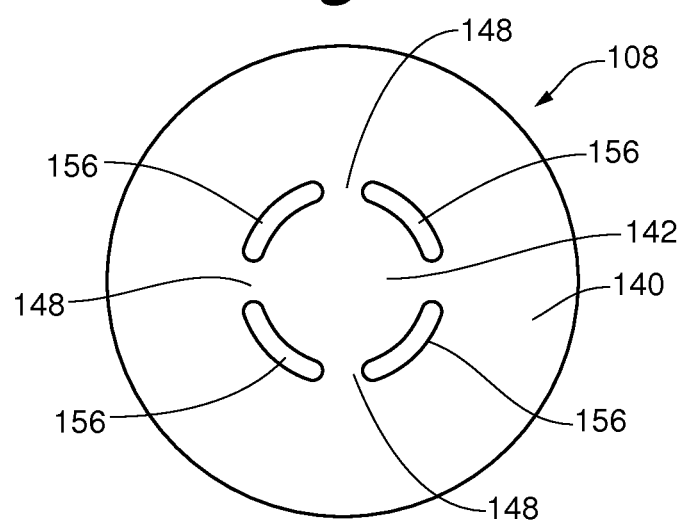
FIG. 19 is a plan view of annular conjunctival cover and an attached lens portion attached to the annular conjunctival cover wherein the lens portion neither underlies nor overlies the conjunctival cover.

Referring now to FIG. 19, another embodiment of coupled corneal conjunctival lens system 108 is depicted. In the depicted embodiment, coupled central lens portion 142 is coupled to conjunctival cover portion 140 by attachment members 148. Attachment members 148 are separated by and adjacent to openings 156.

Referring generally to FIG. 1-10, conjunctival cover 20 according to an embodiment of the invention, generally includes annular shell 22 presenting central opening 24. Annular shell 22 is formed of a hydrophilic or non-hydrophilic flexible material similar to those used in the manufacture and construction of soft contact lenses. Conjunctival cover 20 is utilized in relation to an eye 26. Eye 26 generally includes sclera 28, conjunctiva 30, cornea 32, limbus 34 and eyelids 36. The sclera is the structural white portion of the eye that forms the majority of the eyeball. Conjunctiva 30 overlies the sclera and includes palpebral conjunctiva 40 and bulbar conjunctiva 42. Palpebral conjuctiva 40 and bulbar conjunctiva 42 meet at fornices 44. Cornea 32 is the clear front part of the eye and is generally dome shaped in structure. Limbus 34 is the juncture between the edge of the cornea 32 and sclera 28. Conjunctival cover 20 generally covers bulbar conjuctiva 42 while leaving all or a portion of cornea 32 exposed. For this purpose, central opening 24 is positioned to generally coincide with cornea 32. Annular shell 22 of conjunctival cover 20 may be sized to extend into fornices 44 or may be smaller in size.

Figure 3:
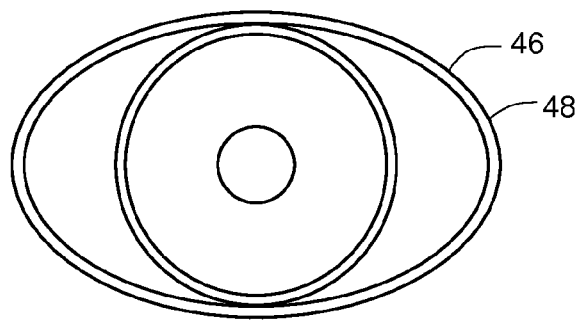
FIG. 3 is a is a schematic depiction of an elliptical annular conjunctival cover applied to an eye according to an example embodiment of the invention.
Figure 4:
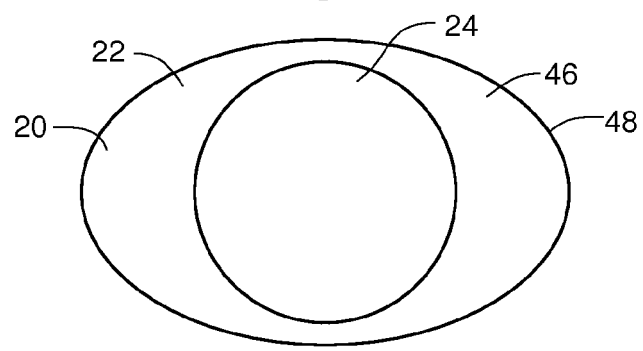
FIG. 4 is a schematic depiction of an elliptical annular conjunctival cover isolated from the eye according to an example embodiment of the invention.

Referring to FIGS. 3 and 4, another embodiment of conjunctival cover 20 is elliptical conjunctival cover 46. Elliptical conjunctival cover 46 includes annular shell 22 having generally elliptical peripheral margin 48. Elliptical conjunctival cover 46 may be sized so that elliptical peripheral margin 48 is generally coincident with eyelid margins 38. Accordingly, elliptical peripheral margin 48 may extend partially under eyelid margins 38 or may be slightly smaller than the space bounded by eyelid margins 38 when eye 26 is open.

Referring now to FIG. 5, another embodiment of conjunctival cover 20 is depicted. Dual ring conjunctival cover 50 generally includes inner ring 52, outer ring 54, nasal cover portion 56 and temporal cover portion 58. Inner ring 52 approximates the corneal diameter being slightly larger or slightly smaller than the limbus. Outer ring 54 is larger than inner ring 52 and may be sized to extend partially or completely into fornices 44. Inner ring 52, outer ring 54, nasal cover portion 56 and temporal cover portion 58 together define arcuate openings 60. Arcuate openings 60 include superior arcuate opening 62 and inferior arcuate opening 64. Inner ring 52, outer ring 54, nasal cover portion 56 and temporal cover portion 58 may be integrally formed, for example, by a molding process or may be overmolded or otherwise assembled of separate structures.

Referring now to FIG. 7, another embodiment of conjunctival cover 20 is depicted. Partial inner ring conjunctival cover 66 generally includes outer ring 68, nasal inner ring segment 70, temporal inner ring segment 72, nasal cover portion 56 and temporal cover portion 58. These structure together define central opening 74 which includes superior opening portion 76, inferior opening portion 78 and central opening portion 80. Accordingly, when placed upon the eye, partial inner ring conjunctival cover 66 generally covers the nasal and temporal conjunctiva while not covering the superior and inferior conjunctiva which are covered by eyelids 36.

Conjunctival cover 20 may also include other fenestrations beyond those identified herein.

Figure 8:
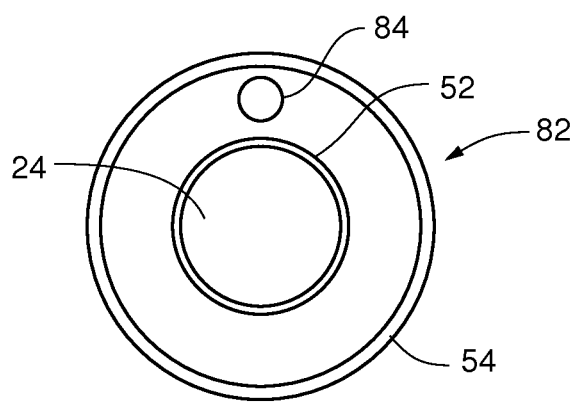
FIG. 8 is a schematic depiction of a conjunctival cover having a drug reservoir to support drug delivery capability according to an example embodiment of the invention.

Referring now to FIG. 8, another embodiment of conjunctival cover 20 is depicted. Drug delivery conjunctival cover 82 can be similar in structure to any of the above described conjunctival covers 20 but is adapted for drug delivery.

According to an embodiment depicted in FIG. 8, drug delivery conjunctival cover 82 includes first drug reservoir 84, second drug reservoir 86 and third drug reservoir 88. Drug delivery conjunctival cover 82 may include one or more drug reservoirs 90. Drug reservoirs 90 may be formed as cavities within drug delivery conjunctival cover 82 which are bounded by a material that is bio-absorbable or bio-degradable in the eye environment. A wall thickness of first drug reservoir 84, second drug reservoir 86 and third drug reservoir 88 may vary in order to facilitate timed release of drug dosages. The first drug reservoir may have a thinner wall that is breached by bio-absorption or biodegradation sooner than the thicker walls of second drug reservoir 86 or third drug reservoir 88.

Drug delivery conjunctival cover 82 may also be formed of a hydrophilic material that absorbs an aqueous solution of a drug to be released for later diffusion into the ocular conjunctival environment. Thus, drug delivery conjunctival cover 82 may be formed of a poly-HEMA or another hydrophilic material known to those skilled in the contact lens arts.

Figure 9:
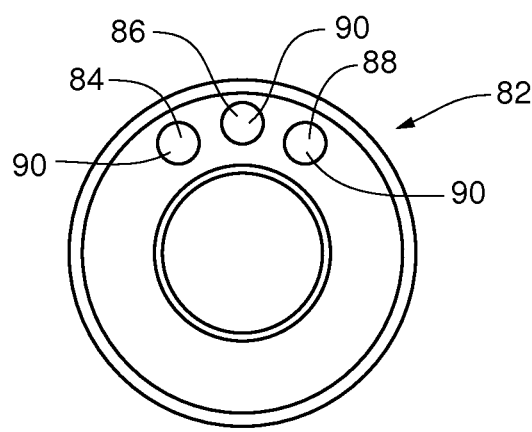
FIG. 9 is a schematic depiction of a conjunctival cover having multiple drug reservoirs to support drug delivery capability according to an example embodiment of the invention.
Figure 10:
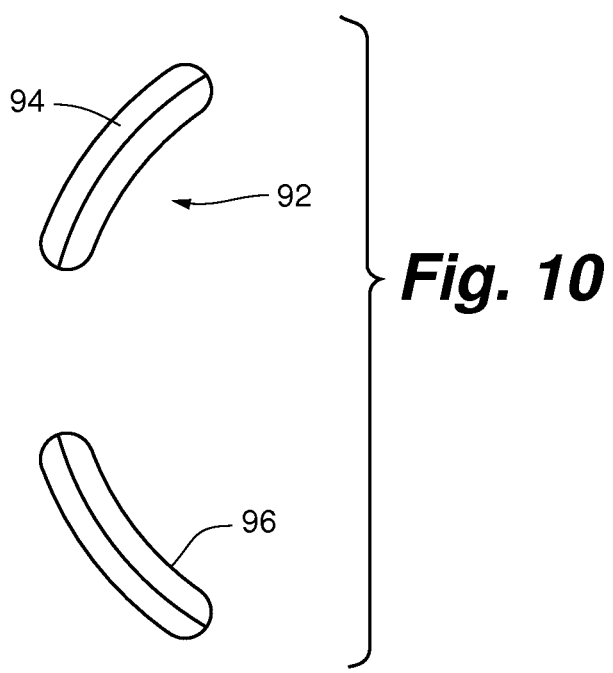
FIG. 10 is a schematic depiction of a conjunctival cover having multiple layers according to an example embodiment of the invention.

Referring now to FIG. 9, another embodiment of conjunctival cover 20 is depicted in cross-section. Multi-layer conjunctival cover 92 includes at least first layer 94 and second layer 96. Multi-layer conjunctival cover 92 may have two or more layers of similar or different construction materials.

Drugs to be delivered by drug delivery conjunctival cover 82 may include but are not limited to antibiotics, steroids, glaucoma medications, antiviral medications, antifungal medications, NSAIDs, surface lubricants and anti-inflammatories such as cyclosporine.

Drug delivery conjunctival cover 82 may also be utilized to deliver nano-technology substances into the eye.

According to another example embodiment the invention includes a method of treating an eye, including applying an annular conjunctival cover to the eye by retracting the eyelids and placing the annular conjunctival cover on a bulbar conjunctiva of the eye while leaving a cornea of the eye substantially uncovered; and releasing the eye lids.

The method may further include incorporating a drug into the annular conjunctival cover prior to application.

The method may further include incorporating the drug into the annular conjunctival cover by exposing the annular conjunctival cover to the drug in solution or suspension such that the drug is absorbed into the annular conjunctival cover.

The method may further include incorporating the drug into the annular conjunctival cover by inserting the drug into a drug reservoir incorporated in the annular conjunctival cover.

The method may further include inserting multiple drugs into multiple separate drug reservoirs incorporated in the annular conjunctival cover.

According to another embodiment, the invention includes a method of treating an eye including applying a conjunctival cover portion 102 to an eye and applying a central contact lens portion 104 to an eye and facilitating tear pumping by the relationship between the conjunctival cover portion 102 and central contact lens portion 104.

According to another embodiment of the invention, the method may be practiced wherein the central contact lens portion 104 is structurally separate from the conjunctival cover 102 and the method may further include applying the central contact lens portion 104 to the eye prior to and partially underlying conjunctival cover 102.

According to another embodiment of the invention, the method may be practiced wherein the central contact lens portion 104 is structurally separate from the conjunctival cover 102 and wherein the method further includes applying the central contact lens portion 104 to the eye after and partially overlying the conjunctival cover 102.

According to another embodiment of the invention, the method may be practiced wherein the central contact lens portion 104 is structurally joined to the conjunctival cover 102 and the method further includes applying the central contact lens portion 104 and the conjunctival cover 102 to the eye as a unit.

According to another embodiment of invention, the central lens portion is structurally joined to the conjunctival cover and the method further includes selecting an arrangement of attachment members 148 joining the central contact lens to the conjunctival cover to be symmetrically arranged whereby tear pumping is facilitated.

According to another embodiment of the invention, central contact lens portion 104 is structurally joined to conjunctival cover 102 and the method further includes selecting attachment members 148 to be arranged to join central contact lens 104 to conjunctival cover 102 asymmetrically whereby tear pumping is facilitated.

In operation, various embodiments of conjunctival cover 20 are applied to conjunctiva 30 in a similar fashion to the application of a soft contact lens or a sclera contact lens. Various embodiments of conjunctival cover 20 may be applied to eye 26 by the patient or by a health care professional. Eyelids 36 are pulled open by using the fingers near the eyelids margins 38 and conjunctival cover 20 is placed upon the eye at least partially covering the conjunctiva 30. As discussed above, various embodiments of conjunctival cover 20 may partially or completely cover the conjunctiva 30 while partially or completely exposing the cornea 32. Various embodiments of conjunctival cover 20 trap mucin and other tear film components between conjunctival cover 20 and conjunctiva 30. The tear film also covers the external surface of conjunctival cover 20. Upon blinking, eyelids 36 and in particular eyelid margins 38 pass over conjunctival cover 20 and both wipes tear film components on the surface of conjunctival cover 20 onto cornea 32 and also squeezes or massages tear film components between conjunctival cover 20 and conjunctiva 30 onto cornea 32.

Elliptical conjunctival cover 46 covers conjunctiva 30 substantially between eyelid margins 38. Dual ring conjunctival cover 50 is placed on eye 26 so that nasal cover portion 56 covers nasal palpebral conjunctiva 40 while temporal cover portion 58 covers the temporal bulbar conjunctiva 42.

Partial inner ring conjunctival cover 66 is placed on eye 26 so that nasal cover portion 56 covers nasal bulbar conjunctiva 40 while temporal cover portion 58 covers temporal bulbar conjunctiva 42.

Drug delivery conjunctival cover 82 is placed on eye 26 where drugs absorb into drug delivery conjunctival cover 82 diffuse out into eye 26 and surrounding structures.

In the case of drug delivery conjunctival cover 82 having first drug reservoir 84 and optionally second drug reservoir 86 and third drug reservoir 88, drug reservoirs 90 dissolve at planned rate to provide time release of contained drugs into the eye.

Referring to FIGS. 11-19, in operation, corneal conjunctival contact lens system 100 is applied on the eye. Referring to FIG. 11, uncoupled corneal conjunctival lens system 106, for example, may be applied by first applying conjunctival cover 102 followed by central lens portion 104.

According to another embodiment, uncoupled corneal conjunctival lens system 106 can be applied as in FIG. 12. Accordingly, central lens portion 104 is applied to the cornea of the eye followed by conjunctival cover 102.

Referring to FIG. 13, according to another example embodiment, uncoupled corneal conjunctival lens system 106 may be applied to the eye by applying either conjunctival cover 102 or central lens portion 104 to the eye first followed by the other of conjunctival cover 102 and central lens portion 104.

Referring again to FIG. 11, overlying portion 114 of central lens portion 104 extends beyond central opening 116 and thus overlies conjunctival cover 102.

Referring again to FIG. 12, underlying central lens portion 122 of central lens portion 104 underlies conjunctival cover 102 according to this example embodiment. In any of the discussed embodiments, optical zone 128 generally overlies an optical axis of the eye while peripheral zone 130 is peripheral to optical zone 128.

Referring again particularly to FIG. 13, intraopening central lens portion 132 is sized to fit within central opening 134. Accordingly, a gap exists between intraopening central lens portion 132 and conjunctival cover 102 according to this embodiment of the invention.

Referring now to FIGS. 14-19, coupled corneal conjunctival lens system 108 is applied to the eye as a unit.

Referring to FIG. 14, posterior coupled corneal conjunctival lens 144 is applied to the eye as a unit. As the eyelid passes over, conjunctival cover portion 140 and coupled central lens portion 142, it is expected that the tears will be tears are pumped from beneath conjunctival cover portion 140 between conjunctival cover portion 140 and coupled central lens portion 142 and then out to the anterior surface.

Referring to FIG. 15, anterior coupled corneal conjunctival lens 150 is applied to the eye as a unit. As the eyelids pass over anterior central lens portion 152 and conjunctival cover portion 154, it is expected that the tears will be pumped from beneath conjunctival cover portion 154 between anterior central lens portion 152 and conjunctival cover portion 154 onto the anterior surface of anterior central lens portion 152 and conjunctival cover portion 154.

Referring now to FIG. 19, coupled corneal conjunctival lens system 108 as in the depicted embodiment, is applied to the eye as a unit. Coupled central lens portion 142 is coupled to conjunctival cover portion 140 by attachment members 148. Openings 156 are located adjacent to and between attachment members 148.

It is expected that the movement of eyelids during blinking will pump tears from beneath conjunctival cover portion 140 and coupled central lens portion 142 through openings 156 to the anterior of coupled central lens portion 142 and conjunctival cover portion 140. It is also expected, in the case of uncoupled corneal conjunctival lens system 106, that similar tear pumping will occur.

According to embodiments of the invention, conjunctival cover 102 and central lens portion 104 may be removed in a similar fashion to soft contact lenses.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

The invention claimed is:

1. A contact lens system, comprising:
   a peripheral conjunctival cover portion including a shell curved and sized to substantially overly a conjunctiva of an eye and defining a full thickness central opening therethrough, the central opening being positioned within the conjunctival cover and sized to expose at least a portion of a cornea of the eye; and
   a central contact lens portion positioned at the central opening;
   wherein the central contact lens portion is coupled to the conjunctival cover portion by attachment members.

2. The contact lens system as claimed in claim 1, wherein the central contact lens portion is larger in diameter than the central opening and partially overlies the conjunctival cover when on the eye.

3. The contact lens system as claimed in claim 1, wherein the central contact lens portion is larger in diameter than the central opening and partially underlies the conjunctival cover when on the eye.

4. The contact lens system as claimed in claim 1, wherein the central contact lens portion is smaller in diameter than the central opening and fits within the central opening when on the eye.

5. The contact lens system of claim 1, wherein the attachment members are radially symmetrically arranged.

6. The contact lens system of claim 1, wherein the attachment members are radially asymmetrically arranged.

7. The contact lens system of claim 1, wherein the central contact lens portion partially underlies the conjunctival cover portion.

8. The contact lens system of claim 1, wherein the central contact lens portion partially overlies the conjunctival cover portion.

9. The contact lens system of claim 1, wherein the central contact lens portion is smaller in diameter than the central opening and is held within the central opening by the attachment members.

10. A method of treating an eye, comprising:
    applying a conjunctival cover to an eye;
    applying a central contact lens portion to an eye; and
    facilitating tear pumping by the relationship between the conjunctival cover portion and the central contact lens portion;
    wherein the central contact lens portion is structurally joined to the conjunctival cover by attachment members.

11. The method as claimed in claim 10, wherein the central contact lens portion is structurally joined to the conjunctival cover and the method further comprising applying the central contact lens portion and the conjunctival cover to the eye as a unit.

12. The method as claimed in claim 10, further comprising selecting attachment members joining the central contact lens to the conjunctival cover to be symmetrically arranged whereby tear pumping is facilitated.

13. The method as claimed in claim 10, further comprising selecting attachment members joining the central contact lens to the conjunctival cover to be asymmetrically arranged whereby tear pumping is facilitated.

14. A method of treating an eye, comprising:
    applying a conjunctival cover to an eye;
    applying a central contact lens portion to an eye; and
    facilitating tear pumping by the relationship between the conjunctival cover portion and the central contact lens portion;
    wherein the central contact lens portion is structurally separate from the conjunctival cover and the method further comprising applying the central contact lens portion to the eye prior to and partially underlying the conjunctival cover.

* * * * *